(12) United States Patent
Michaeli et al.

(10) Patent No.: US 10,912,941 B2
(45) Date of Patent: Feb. 9, 2021

(54) SYSTEM AND METHOD FOR FEEDBACK-DRIVEN NEUROMODULATION

(71) Applicant: REGENTS OF THE UNIVERSITY OF MINNESOTA, Minneapolis, MN (US)

(72) Inventors: Shalom Michaeli, Minneapolis, MN (US); John T. Vaughan, Minneapolis, MN (US); Silvia Mangia, Minneapolis, MN (US); Lauri Lehto, Minneapolis, MN (US); Matthew Johnson, Minneapolis, MN (US); Julia Slopsema, Minneapolis, MN (US); Olli Gröhn, Minneapolis, MN (US); Gregory F. Molnar, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 272 days.

(21) Appl. No.: 15/863,288

(22) Filed: Jan. 5, 2018

(65) Prior Publication Data
US 2018/0185649 A1    Jul. 5, 2018

Related U.S. Application Data

(60) Provisional application No. 62/442,875, filed on Jan. 5, 2017.

(51) Int. Cl.
*A61N 1/36*    (2006.01)
*A61N 1/05*    (2006.01)

(52) U.S. Cl.
CPC ....... *A61N 1/36139* (2013.01); *A61N 1/0534* (2013.01); *A61N 1/0551* (2013.01);
(Continued)

(58) Field of Classification Search
CPC ................ A61N 1/0534; A61N 1/0551; A61N 1/36062; A61N 1/36064; A61N 1/36067; A61N 1/36139
See application file for complete search history.

(56) References Cited

U.S. PATENT DOCUMENTS 8,380,314 B2 * 2/2013 Panken .............. A61N 1/36139
607/45
8,788,044 B2 * 7/2014 John .................. A61N 1/36082
607/46

(Continued)

OTHER PUBLICATIONS

Grossman et al. "Noninvasive Deep Brain Stimulation via Temporally Interfering Electric Fields" Elsevier Inc., Jun. 1, 2017, Cell 169, 30 pages (pp. 1029-1041, e1-e7, Supplemental Figures 9 pages). http://dx.doi.org/10.1016/j.cell.2017.05.024.

(Continued)

*Primary Examiner* — Amanda K Hulbert
(74) *Attorney, Agent, or Firm* — Quarles & Brady LLP

(57) ABSTRACT

Systems and methods are provided for neuromodulation with simultaneous stimulation and reception of neuronal response. A closed-loop control system provides the ability to modulate any combination of at least five parameters of stimulation (magnitude, frequency, amplitude, time, and phase) based on any combination of at least five parameters of received signals. The neuromodulation is well-suited for deep brain stimulation (DBS) applications.

17 Claims, 9 Drawing Sheets
(3 of 9 Drawing Sheet(s) Filed in Color)

(52) U.S. Cl.
CPC ...... *A61N 1/36062* (2017.08); *A61N 1/36064* (2013.01); *A61N 1/36067* (2013.01)

(56) References Cited

U.S. PATENT DOCUMENTS

| | | |
|---|---|---|
| 8,956,273 B2 | 2/2015 | Mishelevich et al. |
| 9,020,604 B2 | 4/2015 | Martens |
| 9,126,044 B2 * | 9/2015 | Kramer ................ A61N 1/0551 |
| 9,174,053 B2 | 11/2015 | Zhu |
| 2012/0016435 A1 | 1/2012 | Rom |
| 2015/0157862 A1 | 6/2015 | Greenberg et al. |

OTHER PUBLICATIONS

LaRoy, J.J.L. et al. "Multitine Deep Brain Stimulation Leads to Shape Neural Activation in Three Dimensions" Journal of Medical Devices, 2014; 8(2): 020919-1-020919-2.

Lehto, et al. "Orientation selective deep brain stimulation" Journal of Neural Engineering, (2016) pp. 1-9.

\* cited by examiner

SYSTEM AND METHOD FOR FEEDBACK-DRIVEN NEUROMODULATION

CROSS-REFERENCE TO RELATED APPLICATIONS

The present disclosure is based on, claims priority to, and incorporates herein by reference in its entirety, U.S. Provisional Application Ser. No. 62/442,875, entitled, "SYSTEM AND METHOD FOR FEEDBACK-DRIVEN NEUROMODULATION," filed Jan. 5, 2017.

BACKGROUND

The present disclosure relates generally to neuromodulation and, more particularly, to simultaneous stimulation and reception of neuronal response. A closed-loop control system may be provided with an ability to modulate any combination of multiple parameters of stimulation, for example, including magnitude, frequency, amplitude, time, and/or phase based on any combination of parameters of received signals.

Neurostimulation by the introduction of exogenous electromagnetic signals by means of electrodes or wireless methods has demonstrated and delivered many scientific and therapeutic benefits. This field and the technology and methods supporting it however are in their infancy. Many new means to effect, observe, control and optimize neurostimulation have yet to be developed and applied. Conventional deep brain stimulation ("DBS") devices, for example, are designed such that frequency and amplitude of the pulses used for DBS are adjusted based on the behavior of the patient. However, it would be useful to be able to determine the location of the implanted electrode in the brain based on the response of the neuronal population. In addition, it would be useful to have a device that will allow for the study of neuronal activity in healthy and diseased states (for example epileptic seizures).

Currently, there is no system available for simultaneous stimulation of the nervous system and the signal reception. There is an urgent need for improving quality, safety, and capabilities of the electrodes used for DBS. Development of devices which allow determination of the response of neuronal system during neuromodulation is crucial for neurosurgical protocols as well as for investigation of different disorders including Parkinson's disease and epilepsy.

SUMMARY

Exemplary systems and methods allow for the utilization of electromagnetic (EM) stimulation in pulsed and/or continuous wave configurations for deep brain stimulation ("DBS") or other neuromodulation devices with different waveforms. The stimulation may be combined with simultaneous reception of the neuronal response using phase sensitive detection. In combination with an appropriate detection, this allows detecting response of the neuronal ensemble. The system may include a minimum of three probes. Multichannel electrodes are used for this system in preferred versions. Phase shifters can be utilized for phase adjustment between channels for generating rotating fields. The EM stimulation which allows for modulating both amplitude and frequency of the EM wave is tuned to be sensitive to a large range of different frequencies, and allows for transmitting rotating EM fields, producing selectivity for neuromodulation when transmitting single or multiple frequencies simultaneously. Phase sensitive detection allows for detecting small signals from the nervous system in the presence of overwhelming noise. The lock-in, or phase sensitive, amplifier can be utilized for signal reception. Frequency sensitizers and attenuators are used, and the system includes efficient TR switches. Feedback loops help ensure that the feedback signal is in phase with input signal to monitor detection/reception and to provide passive and/or active control over stimulus placement or modulation.

In accordance with one aspect of the disclosure, a method for neuromodulation is provided that includes receiving signals based on readings of electrical activity in the brain of a subject, evaluating the received signals to determine one or more observed parameters, and determining one or more stimulation parameters based on the observed parameters.

In accordance with another aspect of the disclosure, a method for modulating physiological electrical activity is provided that includes receiving signals based on readings of electrical activity in one or more excitable cells of a subject, evaluating the received signals to determine one or more observed parameters, and determining one or more stimulation parameters based on the observed parameters.

In accordance with yet another aspect of the disclosure, a system for neuromodulation is provided that includes a plurality of electrodes for delivering electromagnetic (EM) signals for the purpose of stimulating neurons. The system is configured to adjust stimulus signals on electrodes for one or more of independent magnitudes, independent phases, independent frequencies, independent spatial fields, and independent timing sequences.

Advantageously, exemplary systems and methods will allow for significant improvement of current DBS devices, which includes their safety, efficiency, and simplification of the neurosurgical procedures.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

DETAILED DESCRIPTION

An exemplary, generalized neuromodulation and measurement system will now be discussed. For the purposes of science, diagnostics and therapeutic intervention, neurons may be stimulated, monitored, measured and modulated though electromagnetic (EM) transductions. These EM transductions can be introduced or received by electrodes or by wireless means. These EM transduction signals can be varied by magnitude, phase frequency, space or time, or in any combination of these independent degrees of freedom, to effect or to research a desired stimulus or response.

Stimulus and measurement functions may be incorporated into a controlled loop or an open loop. In a feedback controlled or closed loop, a stimulus signal or response can be monitored or measured for information input required to control or modulate the stimulus signal or signals. A closed system can be applied to automatically monitoring the neurostimulation result for purposes of neurostimulation regulation, logging, investigation or other applications. This feedback control look may operate continuously or intermittently. Stimulus and measurement may occur simultaneously, or sequentially. Other functions in this feedback control loop may include data logging, signal adjustment or modulation, or prompts for human intervention. Or this system can be open with a human clinician or investigator in the loop.

Figure 1:
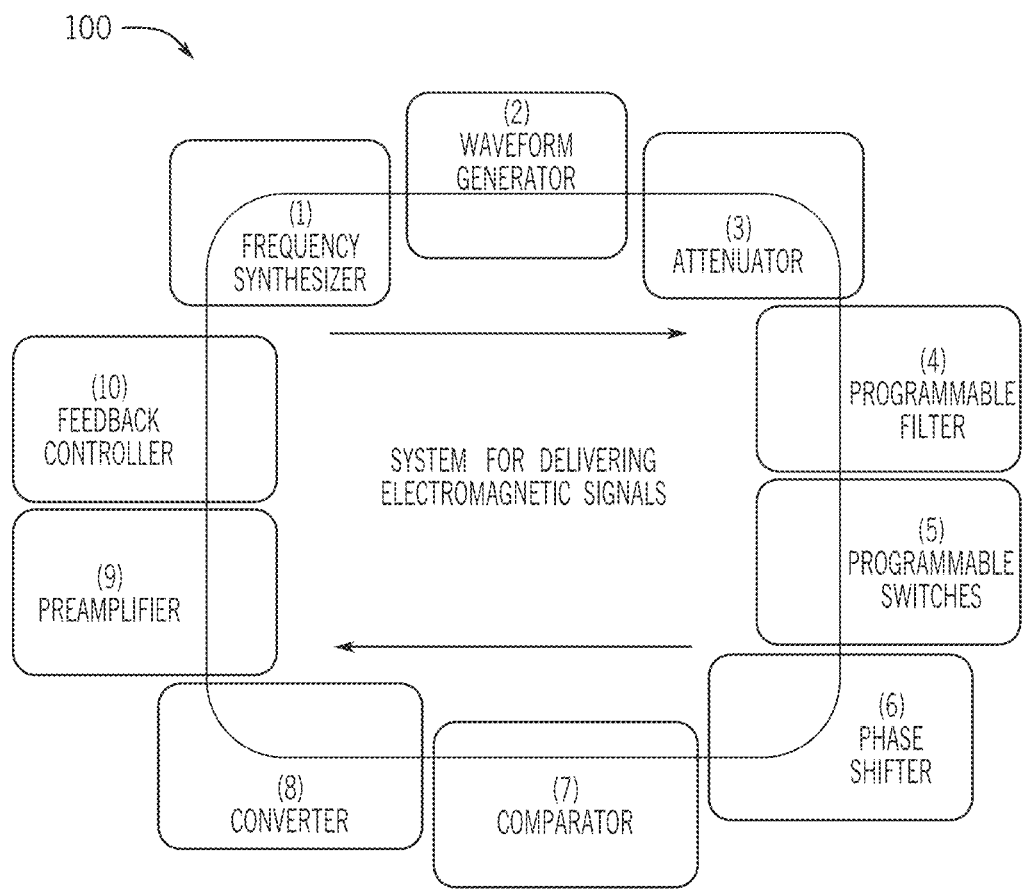
FIG. 1 is a schematic representation of an exemplary system for delivering electromagnetic signals.

Referring to FIG. 1, a system for delivering electromagnetic signals 100 can include but may not be limited to the following components and functions. A programmable frequency synthesizer 1 can be used to establish and control the carrier signal. This frequency synthesizer can be used to set or modulate the signal frequency, to adjust the signal magnitude or phase angle over time. A programmable arbitrary waveform generator 2 can be used to impart and modulate the envelope of the carrier signal to one or more waveforms. These waveforms can be modulated over time. A programmable attenuator 3 can be used to adjust the signal level over time, including turning the signal on and off. A programmable filter 4 can be used to control the bandwidth of the transmit or receive signal. Programmable switches 5 may be used to switch on or off each element over time. A programmable phase shifter 6 can be used to adjust the phase of each signal over time, per signal channel. A comparator 7 can be used to compare two or more signals for feedback control.

A signal acquisition device 8 can be used to convert an acquired signal to a desired form for feedback control, or data analyses, or archiving. A pre amplifier 9 can be used to amplifies the receive signal. A computer 10 can be used for programmable data acquisition or feedback control.

Figure 2:
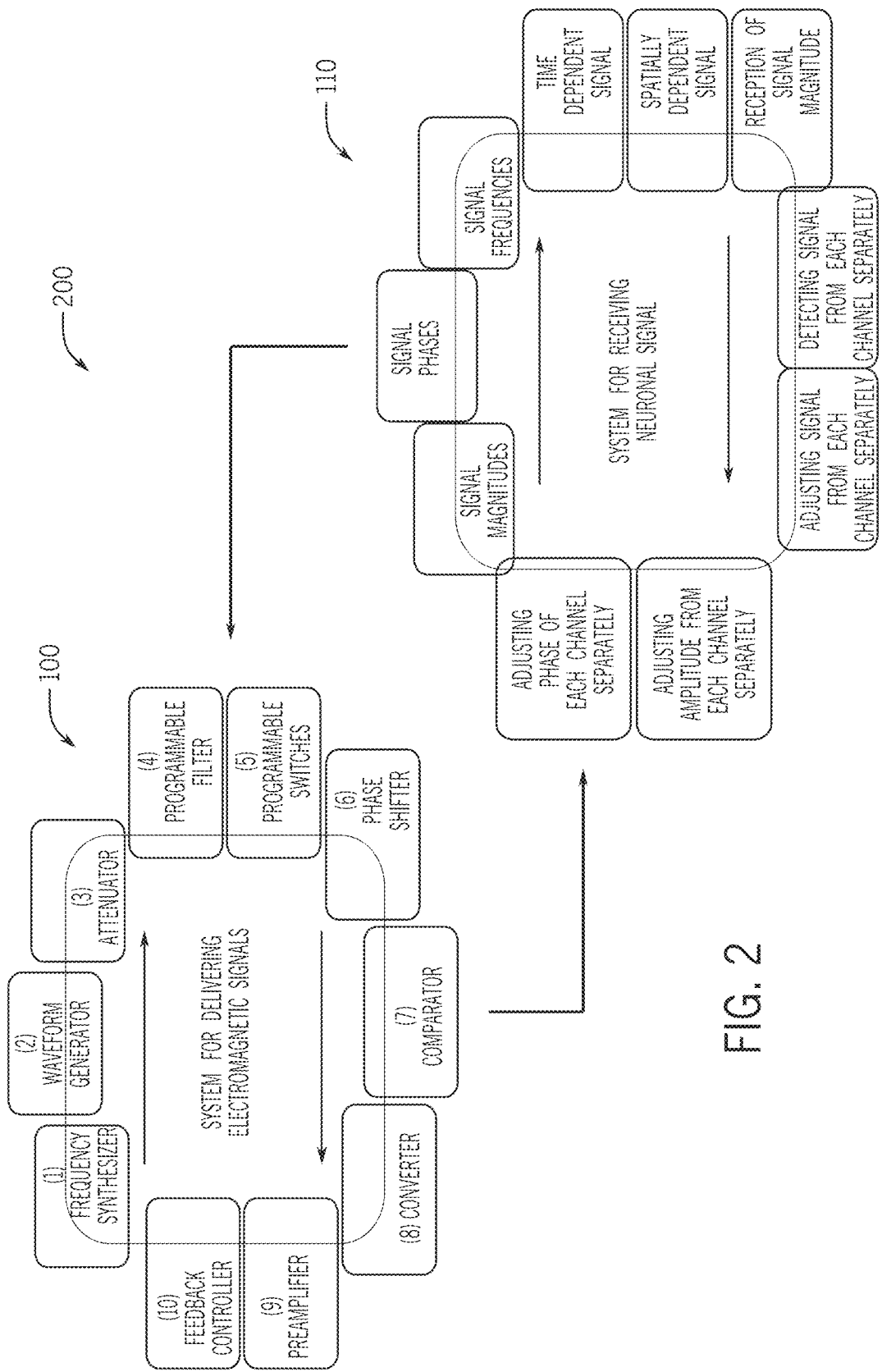
FIG. 2 is a schematic representation of an exemplary neuromodulator, with the exemplary system for delivering electromagnetic signals of FIG. 1, along with a representation of an exemplary system for receiving neuronal signals.

Referring to FIG. 2, an exemplary neuromodulation and measurement system 200 can include the system for delivering electromagnetic signals 100, described above, and a system for receiving neuronal signals 110. The system for receiving neuronal signals can be able to receive/recognize/discern signal magnitudes, signal phases, signal frequencies, the time dependency of signals, and the spatial dependency of signals. The system for receiving neuronal signals 110 may be configured to detect signals from each channel separately. The system for receiving neuronal signals 110 may additionally be configured to adjust signals from each channel separately. Accordingly, the phases of each channel, and the amplitudes from each channel, may be adjusted separately.

Figure 3:
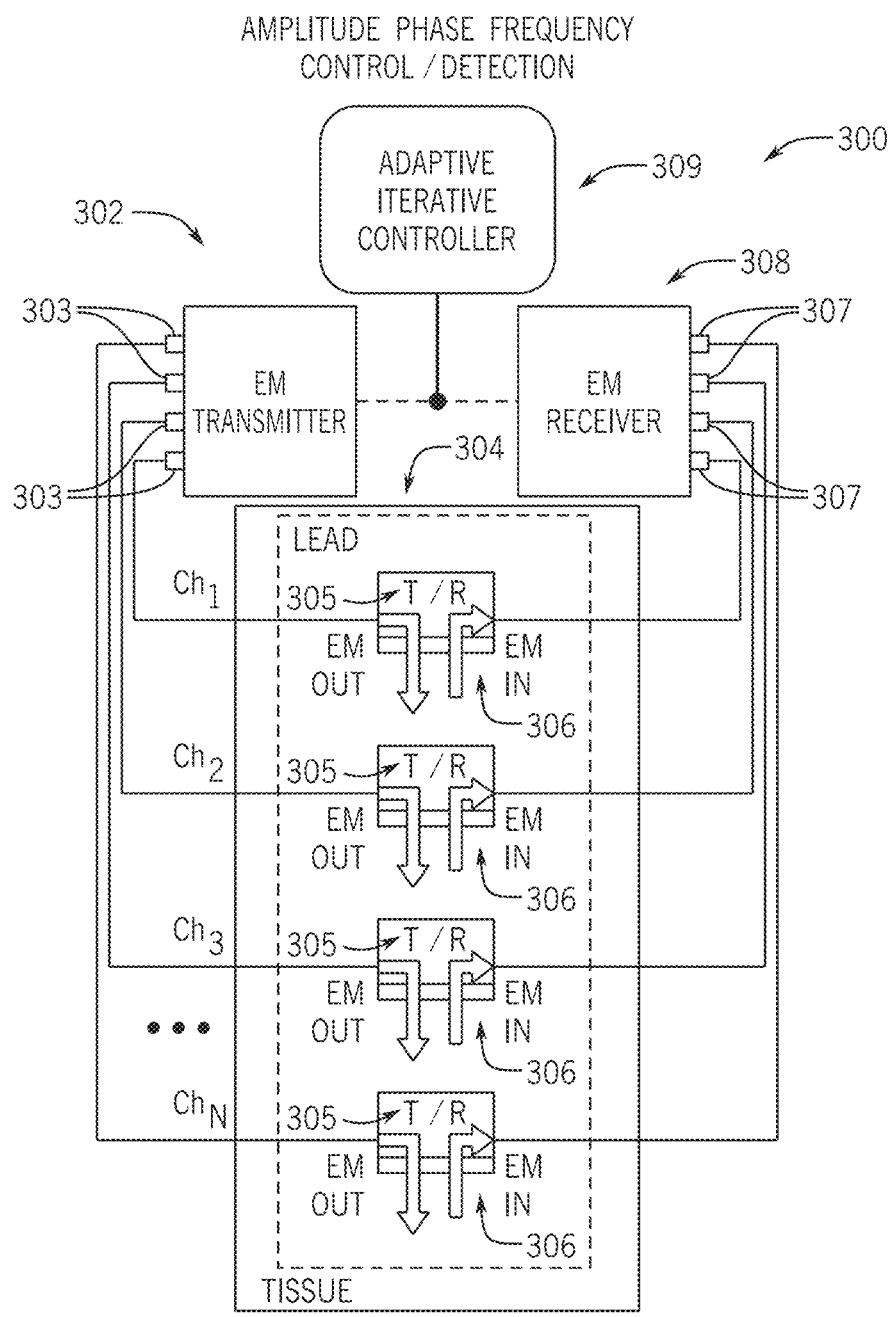
FIG. 3 is a schematic diagram of an exemplary neuromodulation system that provides for control of amplitude, phase, and frequency of the stimulating output EM signal, and detection of the amplitude and phase of the input receive EM signal.
Figure 4:
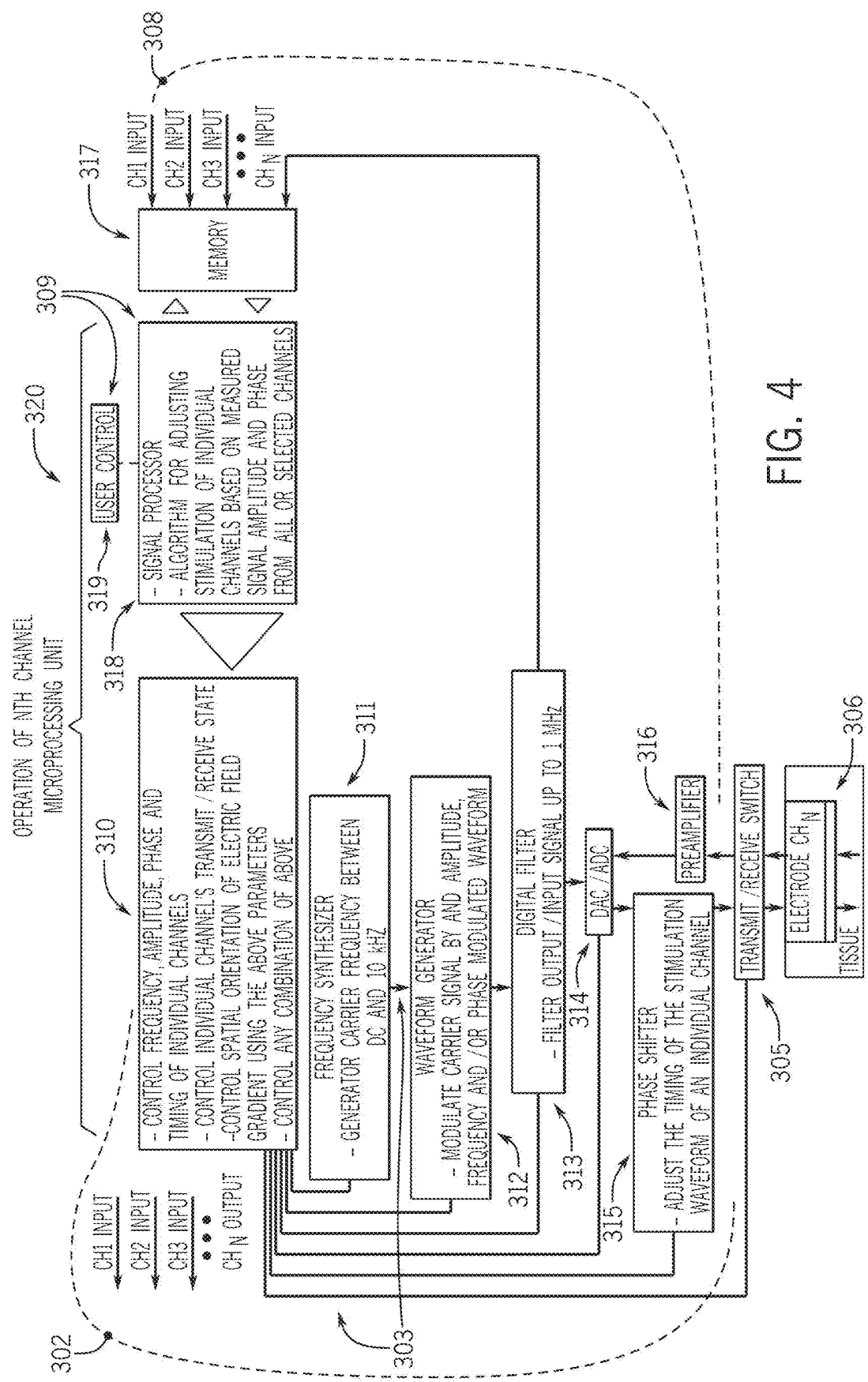
FIG. 4 is a flow chart setting forth some non-limiting steps of an exemplary method of use of the neuromodulation system of FIG. 3.

Referring to FIGS. 3 and 4, another exemplary neuromodulation and measurement system 300 is illustrated. Similar to the neuromodulation and measurement system 200, the neuromodulation and measurement system 300 can control amplitude, phase and frequency of the stimulating output EM signal and detection of the amplitude and phase of the input receive EM signal allows changing frequency, amplitude, phase, and timing of the stimulation from each channel independently, and can allow for generating spatially varying electric field and time varying electric field. Each of these parameters can be varied separately and together. Adjusting frequency in each channel independently in a synchronized way can allow for producing monopolar stimulation. Adjusting phase difference between channels at constant frequency of stimulation can allow for producing spatially selective fields and rotating fields. Sweeping frequency and phase simultaneously can allow for generating time varying gradient of the electric field. By changing sweep function the time dependence of the electric field gradient can be altered. To generate constant gradient of the electric field, the frequency and phase can be changed separately or together. Automatic adjustment can allow for, for example, alternating amplitude of the stimulation with the phase, such that the gradient of the electric field could be constant (as shown in the flowchart).

The neuromodulation and measurement system 300 can include a EM transmitter 302, an EM receiver 308, and an adaptive iterative controller 309. The EM transmitter 302 is configured to produce arbitrary waveforms for N transmit channels 303 with amplitude, phase and frequency modulation individually. The N transmit channels 303 correspond to and communicate with N electrodes 306 on a lead 304. The lead 304 contains the N electrodes 306 and is configured for deep brain stimulation of a subject. The lead 304 can further include N Transmit/Receive (T/R) switches 305 coupled to the N electrodes 306 and corresponding to the N channels 303. T/R stands for the switch between the transmitting of the stimulation to the neuronal system and receiving signals from the neurons.

The EM receiver 308 is configured to receive signals from the neurons through N receive channels 307 corresponding to the N electrodes 306 on the lead 304. The EM receiver 308 is configured to record the amplitude and phase of the measured signals from the N receive channels 307.

The adaptive iterative controller 309 is configured to adjust the amplitude, frequency and/or phase of the selected or all N transmit channels based on the amplitude and phase of the measured signal from selected or all N receive channels. The detected signal response is from the neuronal ensemble, which has a phase and frequency at, for example, the β-band. To maximize the response of the neural ensemble to the stimulation, the frequency and the amplitude of the stimuli can be adjusted first. The frequencies can be varied between 10 to 300 Hz to find an optimal frequency of stimulation, which in some instances may be, for example, around 130 Hz. After adjusting frequency and amplitude, the relative phases of the stimuli can be optimized until a maximal response on the neural system is reached.

Referring now to FIG. 4 specifically, the EM transmitter 302, the EM receiver 308, and the adaptive iterative controller 309 may all be included within a micro processing unit 320. The EM transmitter 302 may include a transmit control unit 310, a frequency synthesizer 311, a waveform generator 312, a digital filter 313, a digital-to-analogue/analogue-to-digital converter 314, and a phase shifter 315. The transmit control unit 310 is configured to control amplitude, frequency and phase of the EM transmit signal of the N transmit channels 303. The frequency synthesizer 311 is configured to generate frequencies between DC and 10 kHz as controlled by the transmit control unit 310. The waveform generator 312 is configured to adjust the amplitude of the EM transmit signal given by the frequency synthesizer 311 as controlled by the transmit control unit 310. The digital filter 313 is configured to filter the transmit signal to desired bandwidth as controlled by the control unit 310. The digital-to-analogue/analogue-to-digital converter (DAC/ADC) 314 is configured to convert the transmit signal to analogue form. The phase shifter 315 is configured to add time delays between the transmit signals as controlled by the transmit control unit 310.

The EM receiver 308 can include a preamplifier 316, the DAC/ADC 314, the digital filter 313, and a memory 317. The preamplifier 316 is configured to amplify the measured signal prior to DAC/ADC 314 and digital filter 313. The DAC/ADC 314 is configured to convert the signal received from the neurons to digital form. The digital filter 313 is configured to filter the received signal to the desired bandwidth. The memory 317 is configured to store and process the measured signal from individual channels.

The adaptive iterative controller 309 can include a signal processor 318 and a user controller unit 319. The signal processor 318 is in communication with the memory 317, the user controller unit 319, and the control unit 310. The signal processor 318 can have an adaptive algorithm to update the EM transmit parameters amplitude, frequency and phase of the control unit 310 based on the measured EM input from the EM receiver 308 stored in memory 317. The stimulation (frequency and amplitude), constant or time-varying, are induced by each contact independently from each other. The frequency (i) and amplitude (ii) in each contact and the relative phases (iii) between contacts are controlled. After inducing the stimulation to the neuronal ensemble, the response (i.e., frequency $f_N$, amplitude $A_N$, and relative phase $F_N$) are recorded and used for adjusting the stimulation to obtain maximal response from the neural ensemble. If the frequency (i) is optimized, while the response of the neurons to the stimulation is low, than the amplitude (ii) of the stimulation can be increased until a larger (maximal) response is recorded. Next, the relative phase difference between contacts can be adjusted accordingly to obtain the desired response from the neuronal populations.

The user controller unit 319 is configured to control the signal processor 318 to adjust the algorithm parameters including stopping the adaptive process to hold current EM transmit parameters or manually inputting the transmit parameters. The user inputs are if the lead is traditional or adaptive. The user can adjust initial parameters such as amplitude, frequency, phases, and waveforms and can have full control over all parameters of the neuromodulation system including active/inactive channels. Output can include the parameters of the local field potential (LFP) response from the neuronal ensemble. The user can select contacts of the lead to determine an activation pattern for the stimulation.

Figure 5:
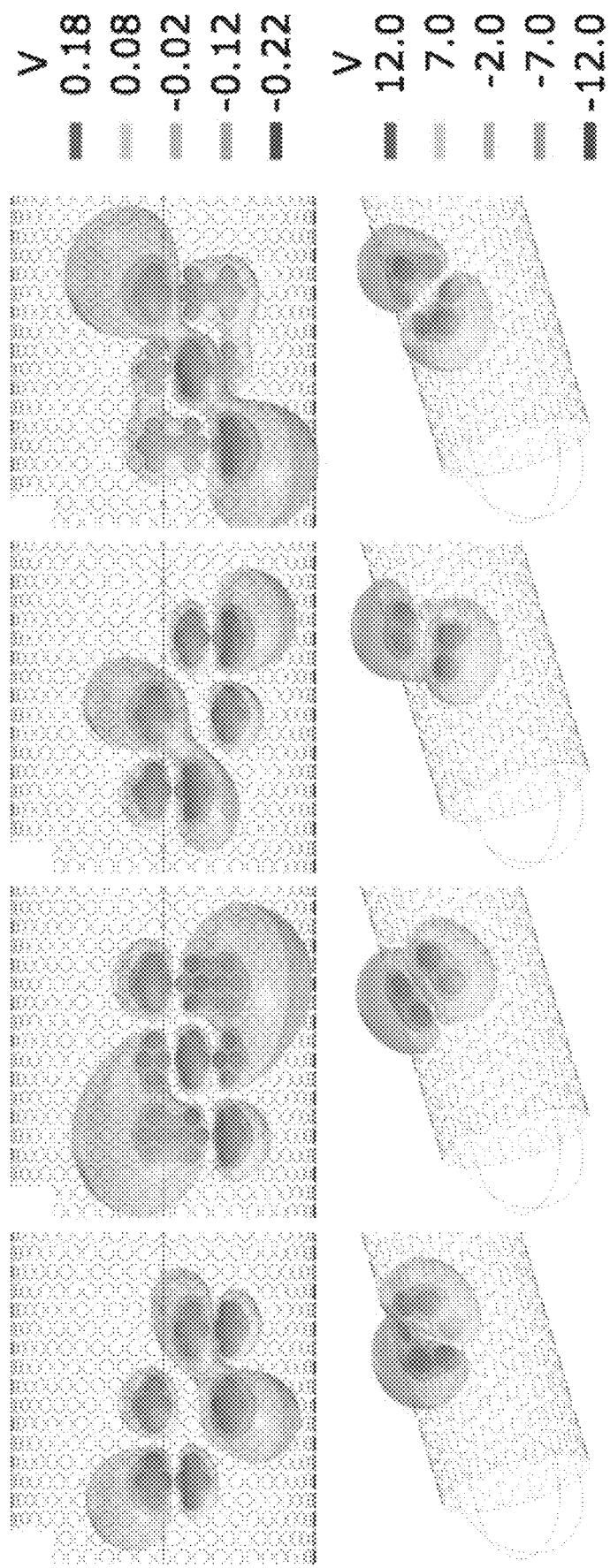
FIG. 5 is an illustration of one design of a contact lead showing rotating field phase steering stimulation using sinusoidal electric fields with the phase differences of 120 degrees between the groups of contacts.

For example, as shown in FIG. 5, the electric potential differences between contacts can be controlled both spatially and temporally, illustrated via phases A-D. The rotating field paradigms can be determined by the user upon selection of the contacts or groups of contacts, as shown in phases E-H. The spatial orientation, duration and distribution of the electric field gradient can be controlled by selecting contacts of the multichannel electrode. The system can search for optimal gradient of electric field generated by different contacts of the multichannel electrode, its spatial and temporal parameters which can provide maximal response of the stimulated ensemble of neurons.

Specifically, with respect to FIG. 5 in phases A-D, the phase differences between the groups of contacts (assuming four contacts in each group) are of 120 degrees. For example: f1=sine (w*t), f2=sine (w*t+2Pi/3)), f3=sine (w*t−2Pi/3)), with the 3×3 matrix design as follows: f3 f2 f1 f2 f1 f3 f1 f3 f2. As an example, the time evolution of the stimulation paradigm from phases A to C represents rotation of the electric field gradient to 180 degrees. Here, 2500 contacts were used for the simulations. The diameter of 0.6 mm of the lead with 50 contacts on the perimeter was assumed. Phases E-H of FIG. 5 show rotating field stimulation paradigms generated using 128-contact lead with the diameter of 0.6 mm and 16 contacts on the perimeter of the lead.

As shown in FIG. 5, cosine amplitude modulation functions can be used for defining the electric field waveforms delivered to each channel according to the Equation:

$$I_i = I_{0i} * \cos(2\pi t/T + \varphi_i),$$

where $I_{0i}$ is the maximal amplitude of electric field and $\varphi_i$ the phases of each channel.

The phase difference between the electrodes could be chosen between 0-2π and may be set to be constant. For rotation around the circle, the phase difference between electrodes may be defined as 2π/3. Next, the phase differences between the channels could be varied and combined with the modulating amplitude of the electric field in each channel; this can form a 2D pattern of the stimulation, e.g., circle or ellipsoid. This can allow for the stimulation of the objects having different shapes or fiber bundles different in their geometry. For example, two cases could be of interest to stimulate: crossing white matter bundles, and crossing individual axons in grey matter.

Figure 6:
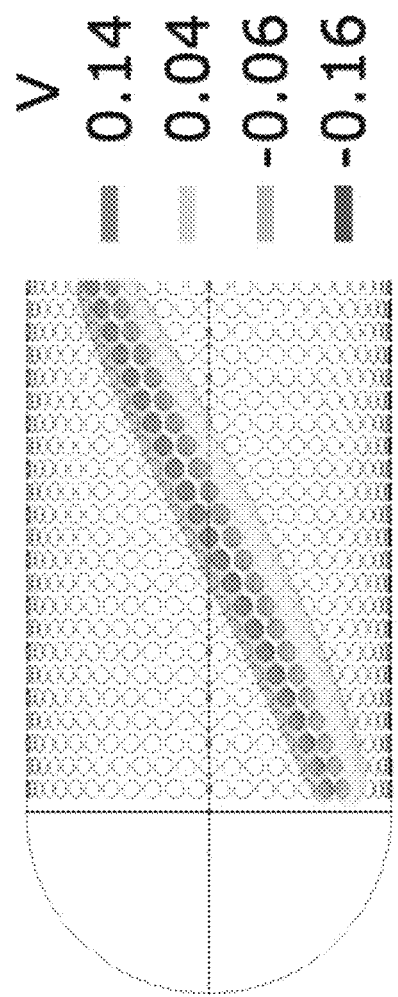
FIG. 6 is an illustration of one design of orientation selective electric field gradient generated using 2500-channel microelectrode with 50 contacts on the perimeter of the lead having diameter of 0.6 mm during two different phases of use.
Figure 6:
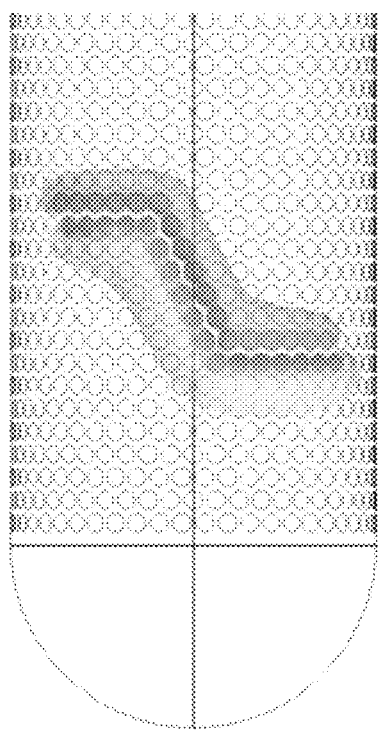

Referring to FIG. 6, provided is an exemplary design of orientation selective electric field gradient generated using 2500-channel microelectrode with 50 contacts on the perimeter of the lead having diameter of 0.6 mm. For demonstration, different channels were selected on the surface of the electrode in the closed proximity to each other. The electric field gradient was generated assuming that same voltage was applied to each contact with no field phase steering. In FIG. 6, a design of the orientation selective gradient is shown. The system allows orienting spatially the direction of electric field gradient by selecting different channels of the lead.

Figure 7A:
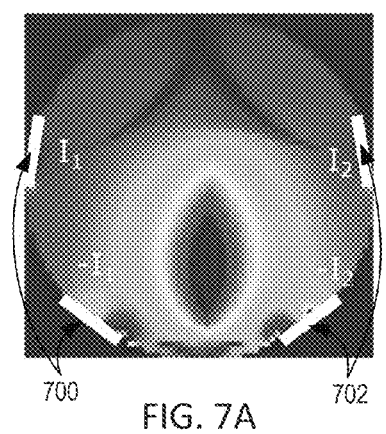
FIG. 7A is an image showing an amplitude of the electric field envelope from four contacts.
Figure 7B:
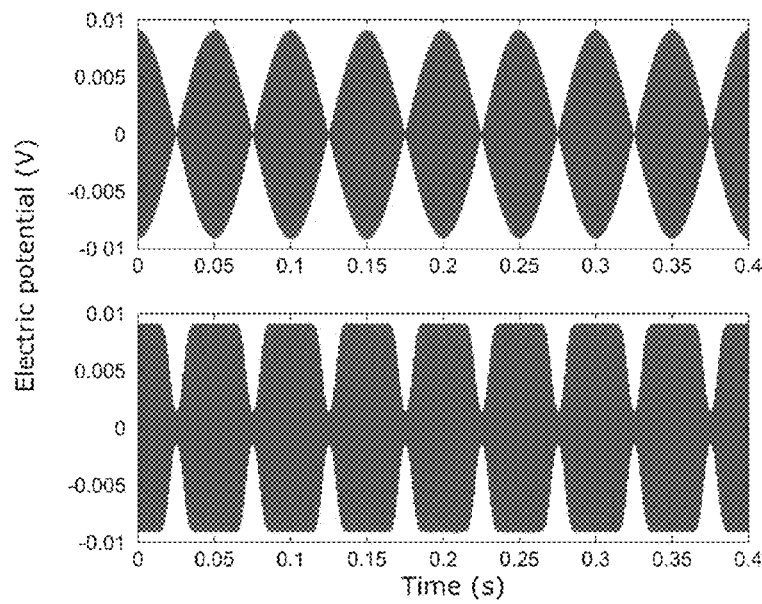
FIG. 7B is a graph showing the electric potential field at the maximum of the envelope shown in FIG. 7A using two different frequencies (upper plot; f=1000 Hz and Δf=20 Hz), and using phase modulation of the other contact pair (lower plot; f=1000, f_p=20 Hz).
Figure 7C:
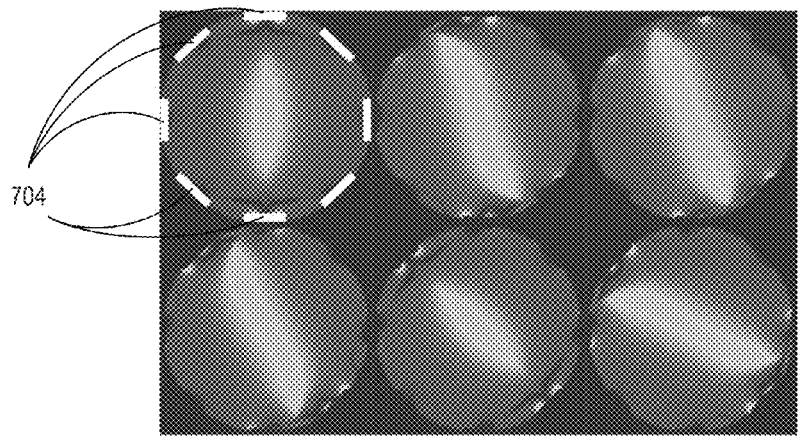
FIG. 7C is an image showing the rotation of the electric field envelope by modulating the amplitude and frequency of eight contacts.

Referring now to FIGS. 7A-7C, non-invasive neuromodulation can be achieved using two pairs of contacts with 1-2 kHz sinusoidal currents flowing between them. By adding a frequency difference $\Delta f$ (smaller than the carrier frequency) to the current flow of the two pairs, the electric field induced by the contact pairs oscillating at $f$ is modulated by an envelope oscillating at $\Delta f$ due to alternating constructive and destructive interference between the pairs of contacts 700, 702 of FIG. 7A. The currents of the pairs can be written $$I_1(t) = I_{0,1} \sin(2\pi f t)$$

$$I_2(t) = I_{0,2} \sin(2\pi [f + \Delta f] t)$$

where t is time, and $I_{0,1}$ and $I_{0,2}$ are the amplitudes of the currents for electrode pair 700 and electrode pair 702, respectively. The location of the amplitude of the electric field envelope is governed by the direction and strength of the individual field of the pairs.

However, in some instances, instead of or in addition to using a frequency difference $\Delta f$ to govern the envelope, phase modulation of one or more of the electric fields of the contact pairs can be used. In these instances, the currents for the two pairs can be written as:

$$I_1(t) = I_{0,1} \sin(2\pi f t + \phi_1(t))$$

$$I_2(t) = I_{0,2} \sin(2\pi f t + \phi_2(t))$$

where $\phi_1$ (t) and $\phi_2$ (t) are time varying phase modulation functions of the pair 700 and the pair 702. The amount of contact pairs is not limited to two and the same principle could be extended to more than 2 pairs. As an example, we set $$\phi_1(t) = 0$$

$$\phi_2(t) = \pi(1 - \alpha(t))$$

where $\alpha(t)$ is a real valued function with values between [0 1], as illustrated in the top graph of FIG. 7B. When $\alpha(t)=0$, $\phi_2$ (t)=$\pi$, the currents and thus the electric fields induced by the two contacts are out of phase by $\pi$ and destructive interference of the fields. When $\alpha(t)=1$, $\phi_2$ (t)=0, the electric fields are in phase leading to maximal constructive interference. The shape of the electric field envelope can be governed by $\alpha(t)$ by setting it to be any real valued function normalized to [0 1]. In bottom graph of FIG. 7B, an example is shown using a function with hyperbolic secant pulsations of the form $$\alpha(t) = \Psi(f_p t) \times \text{sech}(at)$$

where $\Psi(f_p t)$ is the Shah function, $f_p$ is the frequency of pulsation for the pulse and a is a constant describing the shape of the function.

Accordingly, the direction of the electric field can be freely selected or rotated, thereby allowing for Rotating Field Phase Steering (RFPS) paradigms to be used to enhance orientation selectivity of axonal activation. As shown in FIG. 7C, at least four pairs of contacts 704 can be used so that all increments in angle can be described. Choosing the direction or rotating the field direction involves modulating the amplitudes and changing the frequency of the carrier signal depending on the direction of the field. Also the contact pairs can change depending on the direction. Amplitude $I_i$ of contact i can be written $$I_i = I_{0,i} \sin(2[\theta + \phi_i]), \text{ when } \theta + \phi_i \leq \pi$$

$$I_i = -I_{0,i} \sin([2\theta + \phi_i]), \text{ when } \pi < \theta + \phi_i \leq 2\pi$$

where $\theta$ is the direction of the electric field and $\phi_i$ is the initial phase of contact i depending on its location on the circle of electrodes. Rotating electric field can be achieved by modulating $\theta$ in time.

Figure 8:
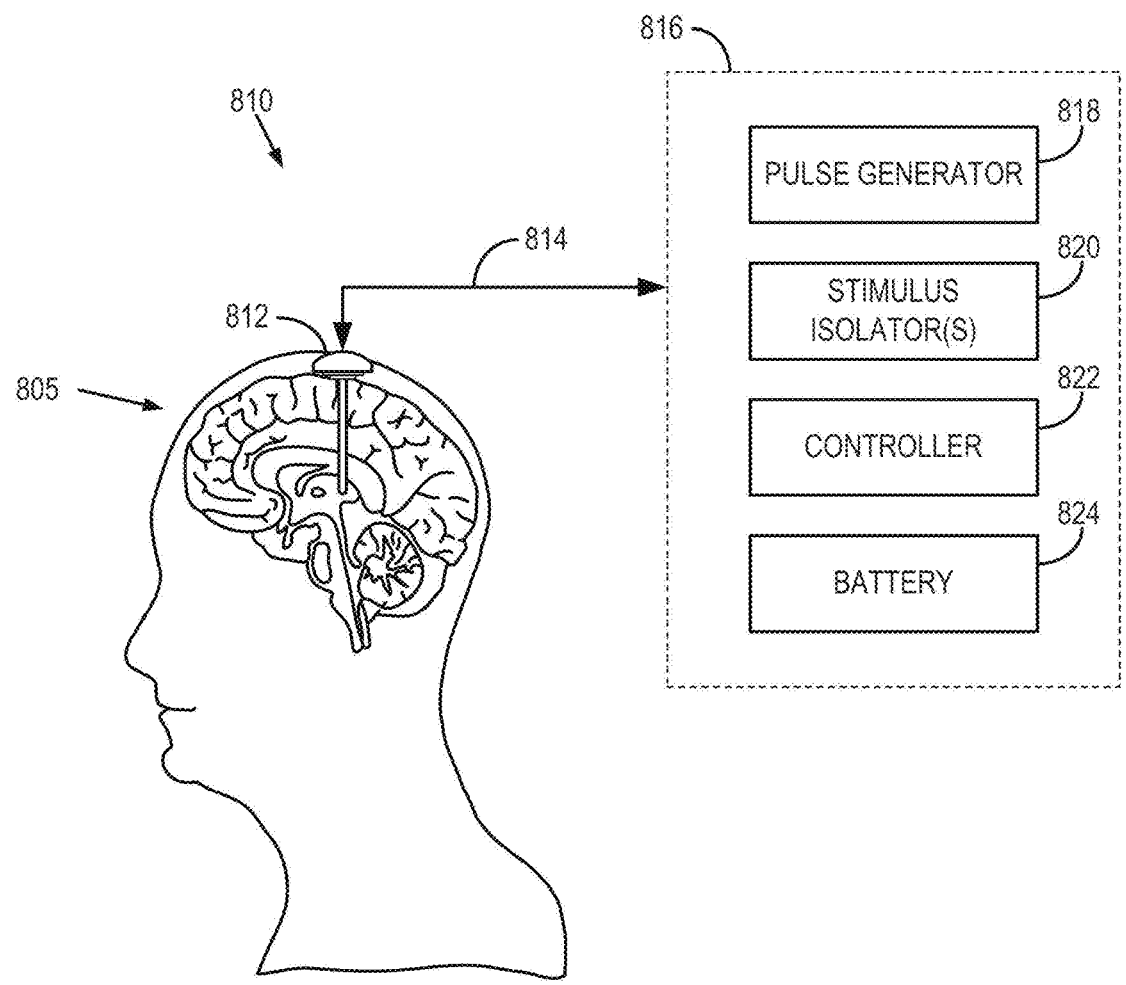
FIG. 8 is an example deep brain system ("DBS") having a multichannel electrode with independently controllable electrode channels that can generate rotating or spatially selective magnetic fields.

Referring now to FIG. 8, a deep brain stimulation ("DBS") system is illustrated that can be used with the systems and methods described herein. The DBS system 810 includes one or more multichannel electrodes 812 that can be operated to generate rotating electromagnetic fields that stimulate neurons regardless of their orientation, or to generate spatially selective electromagnetic fields that preferentially stimulate neurons oriented along a particular direction. In some instances, the DBS system 810 can be a closed loop system. In this regard, feedback, control, and stimulation are coordinated in closed regulation by the system.

The multichannel electrode 812 is implanted in the brain 805 of a subject, and is electrically connected via an insulated cable 814 to a neurostimulator 816, which may be implanted in the subject's torso (e.g., below the subject's clavicle). In some embodiments, the multichannel electrode 812 can wirelessly communicate with the neurostimulator 816. The neurostimulator 816 includes a pulse generator 818, one or more stimulus isolators 820, a controller 822, and a battery pack 824 that powers the DBS system 810.

Figure 9A:
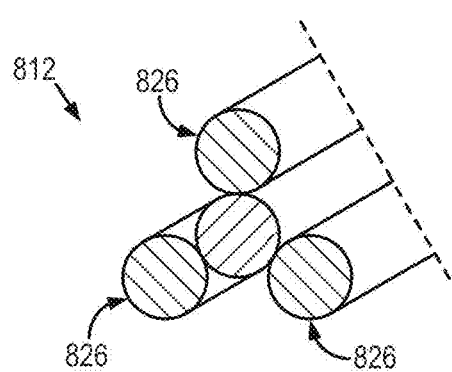
FIG. 9A is an isometric view of an example multichannel electrode.
Figure 9B:
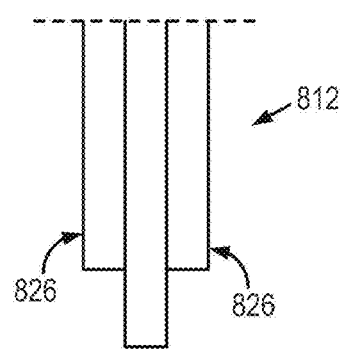
FIG. 9B is a top view of an example multichannel electrode.

One example multichannel electrode 812 is shown in FIGS. 9A and 9B. The multichannel electrode 812 includes several independently controllable and uncoupled electrode channels 826. The multichannel electrode 812 can be composed of a material such as a platinum-iridium alloy, or tungsten.

To control the electromagnetic field orientation in a two-dimensional ("2D") plane located at the tip of the multichannel electrode 812, three or more independently controllable electrode channels can be used. Thus, in some embodiments, the multichannel electrode 812 can be a tripolar electrode to generate orientational and rotating field stimulation in a plane. To control the electromagnetic field orientation in three dimensions, four or more independently controllable electrode channels can be used. The position of the inner channel 826 in FIGS. 9A and 9B, as well as the relative distances between each channel 826, can be varied. As one example, the inner channel 826 can be closed to one of the other three channels 826 shown in FIGS. 9A and 9B. In this example, varying the position of the inner electrode channel 826 relative to the outer electrode channels 826 provides flexibility in to generate asymmetry of the electromagnetic fields.

Figure 9C:
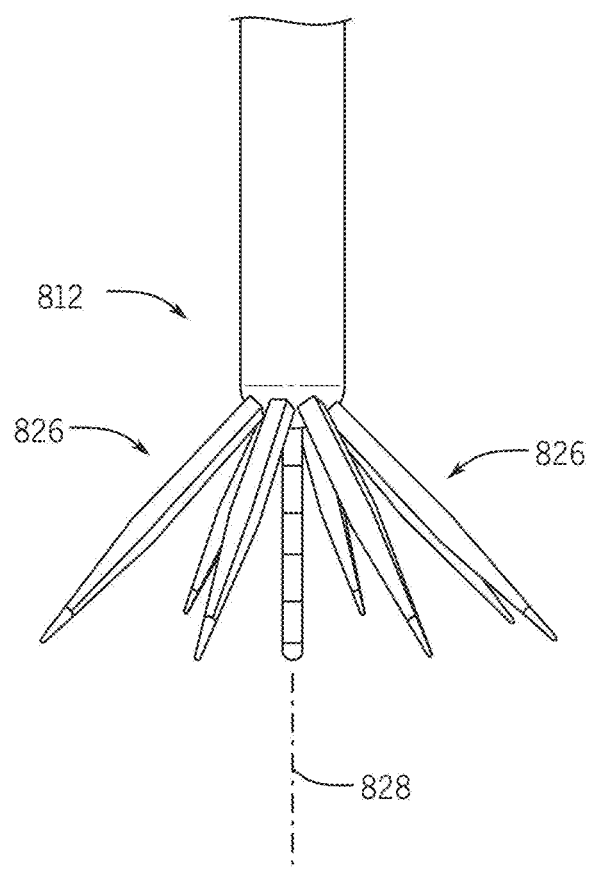
FIG. 9C is an example of a multichannel electrode having multiple tines that are angled away from a longitudinal axis of the multichannel electrode.

Another example multichannel electrode 812 is shown in FIG. 9C. This multichannel electrode 812 includes multiple independently controllable electrode channels 826 that can be angled away from a longitudinal axis 828 of the multichannel electrode 812. An example of such a multi-tined electrode is described by J J L LaRoy, et al., in "Multi-tine deep brain stimulation leads to shape neural activation in three dimensions," Journal of Medical Devices, 2014; 8(2): 020919. It will be understood that a multitude of other suitable multichannel electrodes can be used, and the exemplary multichannel electrodes provided are in no way meant to be limiting.

As mentioned above, the DBS system 810 can include one multichannel electrode 812, but can also include more than one multichannel electrode 812. In this latter configuration, the multiple multichannel electrodes 812 can provide more flexibility to shape the electromagnetic field for selective excitation of particular neuronal populations.

The independently controllable electrode channel design of the multichannel electrode 812 allows for current, or voltage, to be delivered in each channel 826 with different amplitude modulation, frequency modulation, phase modulation, or combinations thereof. Thus, the DBS system 810 allows for the independent control of the amplitude, frequency, and phase of the current, or voltage, in each channel 826. For example, the amplitude, frequency, or phase in a given channel may be constant or modulated according to a channel-specific function. Using this independent control of the individual electrode channels 826 in the multichannel electrode 812, the DBS system 810 can generate rotating electromagnetic fields that are capable of stimulating neurons regardless of their orientation, or can generate spatially-selective electromagnetic fields to preferentially stimulate neurons oriented along specific directions.

The neurostimulator 816 sends signals to each channel 826 in the multichannel electrode 812 to generate electromagnetic fields to stimulate neurons. Each channel 826 of the multichannel electrode 812 can be independently driven under the control of stimulation signals generated by the pulse generator 818 and provided to separate stimulus isolators 820 under control of the controller 822, which may include a digital-to-analog converter.

The controller 822 sends channel-specific control signals to the electrode channels 826, such as the channel-specific control signals discussed above, with reference to Equations 1-9.

It will be understood that the systems and methods described above can be used for modulating physiological electrical activity of organs and tissues other than the brain of a subject. For example, the modulated physiological electrical activity can be in the spine, suitable muscle tissue, or various organs of the subject. Further, the modulation can, for example, be neuromodulation, deep brain stimulation (DBS), epidural electrical stimulation (EES), or any other suitable type of modulation and/or stimulation. Additionally, the modulation of the physiological electrical activity can be used to excite, for example, a neuron or muscle fiber of the subject. The following examples are provided to illustrate potential uses of the systems and methods described herein. These examples are in no way meant to be limiting.

Example 1

Epidural electrical stimulation (EES) can facilitate non-voluntary motor activity and enable volitional control of motor functions loss because of the spinal cord injury (SCI). Specifically, the orientation of spinal cord dorsal structures, with respect to the electrical field, play a critical role in determining motor evoked potentials facilitated via EES. In one example, a swine model was used to investigate the relationship between spinal cord neuroanatomy and EES evoked motor responses due to the similarity to humans in terms of anatomical dimensions, size and orientation of the vertebral bone structures and spinal segments. The protocols for selective stimulation of the dorsal roots afferents were designed based on the anatomical measurements of the swine lumbar spinal cord. The differences between L5–L6 and L1–L4 segments were quantified in terms of spatial orientation of the dorsal roots. This protocol included stimulation with quadrupole electrode with sinusoid waveforms delivered such that allowed change of orientation of the electrical field generated by the multichannel lead, and provided directionally selective or rotating electric field gradients.

It was shown that the orientation of electrical field gradients relative to the dorsal roots entry zone is critical factor to evoke low threshold motor response amplitudes, and that the technique disclosed herein can provide spatially selective epidural stimulation with limited amount of leads as compare to multi-electrode arrays. It was also shown that the spatial orientation of dorsal roots is closely correlates with EES evoked motor responses. Accordingly, the disclosed approach can provide better functional activation of the spinal cord circuitry, and may allow for more versatile spinal cord neuromodulation strategies in clinical practice.

Example 2

Pulse patterns used in deep brain stimulation (DBS) therapy are thought to induce largely non-specific axonal activation surrounding active electrodes. Given the proximity of active electrodes to regions implicated in side effects of DBS as well as the high levels of anisotropy within and surrounding DBS targets, more selective stimulation approaches allow for effective therapies, while minimizing undesired side effects. In some instances, as referenced above, a spatiotemporal approach based on Rotating Field Phase Steering (RFPS) paradigms can be used enhancing orientation selectivity of axonal activation.

RFPS approaches were evaluated using computational tissue conductance models developed in COMSOL and coupled with axonal models in NEURON to estimate axon activation thresholds for (1) a Medtronic 4-annular-contact channel DBS lead and (2) an Abbott 8-contact array with two annular contacts separated by two rows of 3 segmented contacts. Stimulation was applied in varying electrode combinations using phase-offset ($0$-$2\pi$) sinusoids, pulse delayed ($0$-$500$ µs) sinusoids, and biphasic square pulses. Axonal activation thresholds were analyzed for axons radially distributed 1 mm adjacent to the central axis of the leads.

Sinusoids, applied through two adjacent cathodes on the Medtronic lead with no phase-offset and no pulse delay, resulted in lower activation thresholds for axons perpendicular versus parallel to the lead (1:1.65 for sinusoids, 1:1.53 for pulses). In contrast, sinusoids with a phase-offset of $\pi$, pulse delay of 500 µs, and bipolar square pulses between two adjacent contacts revealed lowest thresholds for parallel axons with a threshold ratios of 5.86:1, 5.75:1, and 5.58:1 respectively. Coupling the Abbott DBS lead to the stimulation paradigms described herein using two diagonally-oriented segmented contacts improved orientation selectivity to ±30° relative to the central axis of the lead. Thresholds ratios of 1:4.60 (phase offset=$\pi$) and 0.56:1 (phase offset=0), were found for axons aligned with the active contacts (−30° relative to the lead central axis) compared to axons antiparallel to the active contacts (+60°).

It was thus demonstrated that RFPS combined with multichannel electrodes provides a wide spectrum of variables for more efficient, flexible, and selective neuromodulation, and allow for efficient multifrequency stimulation, thus allowing, while avoiding pathways implicated in side effects.

The present invention has been described in terms of one or more preferred embodiments, and it should be appreciated that many equivalents, alternatives, variations, additions, and modifications, aside from those expressly stated, and apart from combining the different features of the foregoing versions in varying ways, can be made and are within the scope of the invention. The true scope of the invention will be defined by the claims included in any later-filed utility patent application claiming priority from this provisional patent application.

We claim:

1. A method for modulating physiological electrical activity, the method comprising the steps of:
   a. receiving signals based on readings of electrical activity in one or more excitable cells of a subject using a phase-sensitive detection;
   b. evaluating the received signals to determine one or more observed parameters;
   c. determining one or more stimulation parameters based on the observed parameters; and
   d. delivering stimulation according to the one or more stimulation parameters by generating rotating electromagnetic fields in the subject or by inducing orientation selective stimulation in the subject; and
   e. simultaneously with delivering the stimulation, receiving signals based on readings of electrical activity from one or more excitable cells of a subject.

2. The method of claim 1 wherein the physiological electrical activity is in the brain of the subject.

3. The method of claim 1 wherein the physiological electrical activity is in the spine of the subject.

4. The method of claim 2 wherein the modulation of physiological electrical activity is neuromodulation.

5. The method of claim 2 wherein physiological electrical activity is modulated as part of deep brain stimulation (DBS).

6. The method of claim 1 wherein the physiological electrical activity involves at least one of an organ of the subject and a muscle of the subject.

7. The method of claim 1 wherein the one or more excitable cells include at least one of a neuron of the subject and a muscle fiber of the subject.

8. The method of claim 1 wherein delivering stimulation includes simultaneously delivering stimulation using a pattern of multiple frequencies established by controlled waveform delivered to each of a plurality of contacts engaged with the subject.

9. The method of claim 1 wherein delivering stimulation includes delivering stimulation at least one of multiple contacts engaged with the subject as spatially distributed locations in the subject or at multiple frequencies simultaneously using amplitude or phase modulated waveforms.

10. The method of claim 1 wherein delivering the stimulation includes delivering electromagnetic (EM) signals across a plurality of electrodes engaged with the subject and adjusting the delivering of stimulation by adjusting the EM signals for one or more of:
    independent magnitudes;
    independent phases;
    independent frequencies;
    independent spatial fields; and
    independent timing sequences.

11. The method of claim 10 wherein the plurality of electrodes include an array of independent multichannel electrodes in different locations of neuronal pathways in the subject and the delivering stimulation and receiving signals is performed using the plurality of electrodes.

12. The method of claim 10 wherein the plurality of electrodes include tripolar electrodes and delivering the stimulation includes generating orientational or rotating field stimulation in a plane in the subject.

13. The method of claim 10 wherein multiple frequencies are delivered simultaneously to the plurality of electrodes in a pattern of multiple frequencies established using a controlled waveform delivered to each contact of the plurality of electrodes.

14. The method of claim 1 further comprising delivering the stimulation according to the one or more stimulation parameters based on evaluating the received signals.

15. The method of claim 1 further comprising delivering the stimulation to one or more neurons in the brain or spinal cord.

16. The method of claim 15 wherein receiving signals includes acquiring readings of electrical activity in the brain resulting from delivering the stimulation.

17. The method of claim 1 wherein at least one of the observed parameters and the stimulation parameters include one or more of magnitude, frequency, amplitude, time, and phase.

* * * * *

UNITED STATES PATENT AND TRADEMARK OFFICE
CERTIFICATE OF CORRECTION

PATENT NO. : 10,912,941 B2
APPLICATION NO. : 15/863288
DATED : February 9, 2021
INVENTOR(S) : Shalom Michaeli et al.

Page 1 of 1

It is certified that error appears in the above-identified patent and that said Letters Patent is hereby corrected as shown below:

In the Claims

Column 11, Claim 9, Line 40, "subject as spatially" should be --subject at spatially--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*